(12) United States Patent
Zagatsky et al.

(10) Patent No.: US 12,137,890 B2
(45) Date of Patent: Nov. 12, 2024

(54) SURGICAL RETRACTOR, METHODS OF MAKING A SURGICAL RETRACTOR, AND METHODS OF RETRACTING TISSUE

(71) Applicant: Invuity, Inc., San Francisco, CA (US)

(72) Inventors: Vladimir Zagatsky, San Francisco, CA (US); Fernando Erismann, Sacramento, CA (US)

(73) Assignee: Invuity, Inc., San Francisco, CA (US)

( * ) Notice: Subject to any disclaimer, the term of this patent is extended or adjusted under 35 U.S.C. 154(b) by 189 days.

(21) Appl. No.: 17/638,522

(22) PCT Filed: Sep. 18, 2020

(86) PCT No.: PCT/US2020/051673
§ 371 (c)(1),
(2) Date: Feb. 25, 2022

(87) PCT Pub. No.: WO2021/055882
PCT Pub. Date: Mar. 25, 2021

(65) Prior Publication Data
US 2022/0401094 A1     Dec. 22, 2022

Related U.S. Application Data

(60) Provisional application No. 62/902,804, filed on Sep. 19, 2019.

(51) Int. Cl.
*A61B 17/02*        (2006.01)
*A61B 90/30*        (2016.01)

(52) U.S. Cl.
CPC .......... *A61B 17/0218* (2013.01); *A61B 90/30* (2016.02); *A61B 2090/306* (2016.02); *A61B 2217/005* (2013.01)

(58) Field of Classification Search
CPC ............... A61B 17/0218; A61B 90/30; A61B 2090/306; A61B 17/02
(Continued)

(56) References Cited

U.S. PATENT DOCUMENTS

2009/0054853 A1    2/2009  Huyser et al.
2016/0313499 A1*  10/2016  Zagatsky ........... A61B 1/00167

FOREIGN PATENT DOCUMENTS

WO    2015/116724 A1    8/2015
WO    2016/172640 A1   10/2016

OTHER PUBLICATIONS

International Search Report mailed on Mar. 5, 2021, issued in connection with International Application No. PCT/US2020/051673, filed on Sep. 18, 2020, 5 pages.
(Continued)

*Primary Examiner* — Eduardo C Robert
*Assistant Examiner* — Tara Rose E Carter
(74) *Attorney, Agent, or Firm* — McDonnell Boehnen Hulbert & Berghoff LLP

(57) ABSTRACT

In an example, a surgical retractor includes an elongated shaft extending from a first end to a second end, and a retractor blade extending from the second end of the elongated shaft. The elongated shaft defines an internal chamber. The elongated shaft includes a handle portion at the first end of the elongated shaft, a suction conduit in a first lateral portion of the internal chamber, and a light conduit in a second lateral portion of the internal chamber. The suction conduit extends from a suction port at the first end to a suction aperture at the second end. The light conduit extends from a light-input port at the first end to a light aperture at the second end. The suction conduit and the light conduit are
(Continued)

substantially coplanar. The surgical retractor also includes an optical waveguide in the light conduit of the elongated shaft.

20 Claims, 14 Drawing Sheets

(58) Field of Classification Search
USPC .................................................. 600/201–245
See application file for complete search history.

(56) References Cited

OTHER PUBLICATIONS

Written Opinion mailed on Mar. 5, 2021, issued in connection with International Application No. PCT/US2020/051673, filed on Sep. 18, 2020, 8 pages.

\* cited by examiner

SURGICAL RETRACTOR, METHODS OF MAKING A SURGICAL RETRACTOR, AND METHODS OF RETRACTING TISSUE

CROSS REFERENCE TO RELATED APPLICATION

This application is the US national phase under 35 U.S.C. § 371 of International Application No. PCT/US2020/051673, filed Sep. 18, 2020, which claims the benefit of U.S. Provisional Patent Application No. 62/902,804, filed on Sep. 19, 2019, the contents of which are hereby incorporated by reference in their entirety.

FIELD

The present disclosure generally relates to surgical retractors and, more specifically, to surgical retractors having illumination and suction features.

BACKGROUND

A surgical retractor is a surgical instrument used to separate a surgical incision and/or retract tissue to provide access to underlying organs and/or tissue during a surgical procedure. The surgical retractor may include a handle that can be gripped by a medical practitioner and a retractor blade extending from the handle for engaging the tissue to be retracted.

SUMMARY

In an example, a surgical retractor includes an elongated shaft extending from a first end to a second end, and a retractor blade extending from the second end of the elongated shaft. The elongated shaft defines an internal chamber. The elongated shaft includes a handle portion at the first end of the elongated shaft, a suction conduit in a first lateral portion of the internal chamber, and a light conduit in a second lateral portion of the internal chamber. The suction conduit extends from a suction port at the first end to a suction aperture at the second end. The light conduit extends from a light-input port at the first end to a light aperture at the second end. The suction conduit and the light conduit are substantially coplanar between the first end and the second end. The surgical retractor also includes an optical waveguide in the light conduit of the elongated shaft.

In another example, a method of retracting tissue is described. The method can include retracting, using a surgical retractor, tissue to expose a surgical site. The surgical retractor includes an elongated shaft extending from a first end to a second end, and a retractor blade extending from the second end of the elongated shaft. The elongated shaft defines an internal chamber. The elongated shaft includes a handle portion at the first end of the elongated shaft, a suction conduit in a first lateral portion of the internal chamber, and a light conduit in a second lateral portion of the internal chamber. The suction conduit extends from a suction port at the first end to a suction aperture at the second end. The light conduit extends from a light-input port at the first end to a light aperture at the second end. The surgical retractor also includes an optical waveguide in the light conduit of the elongated shaft.

The method can also include, while retracting the tissue, illuminating the surgical site using the optical waveguide. The method can further include, while retracting the tissue, applying suction using the suction conduit to evacuate one or more substances from the surgical site.

The features, functions, and advantages that have been discussed can be achieved independently in various examples or may be combined in yet other examples further details of which can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1A:
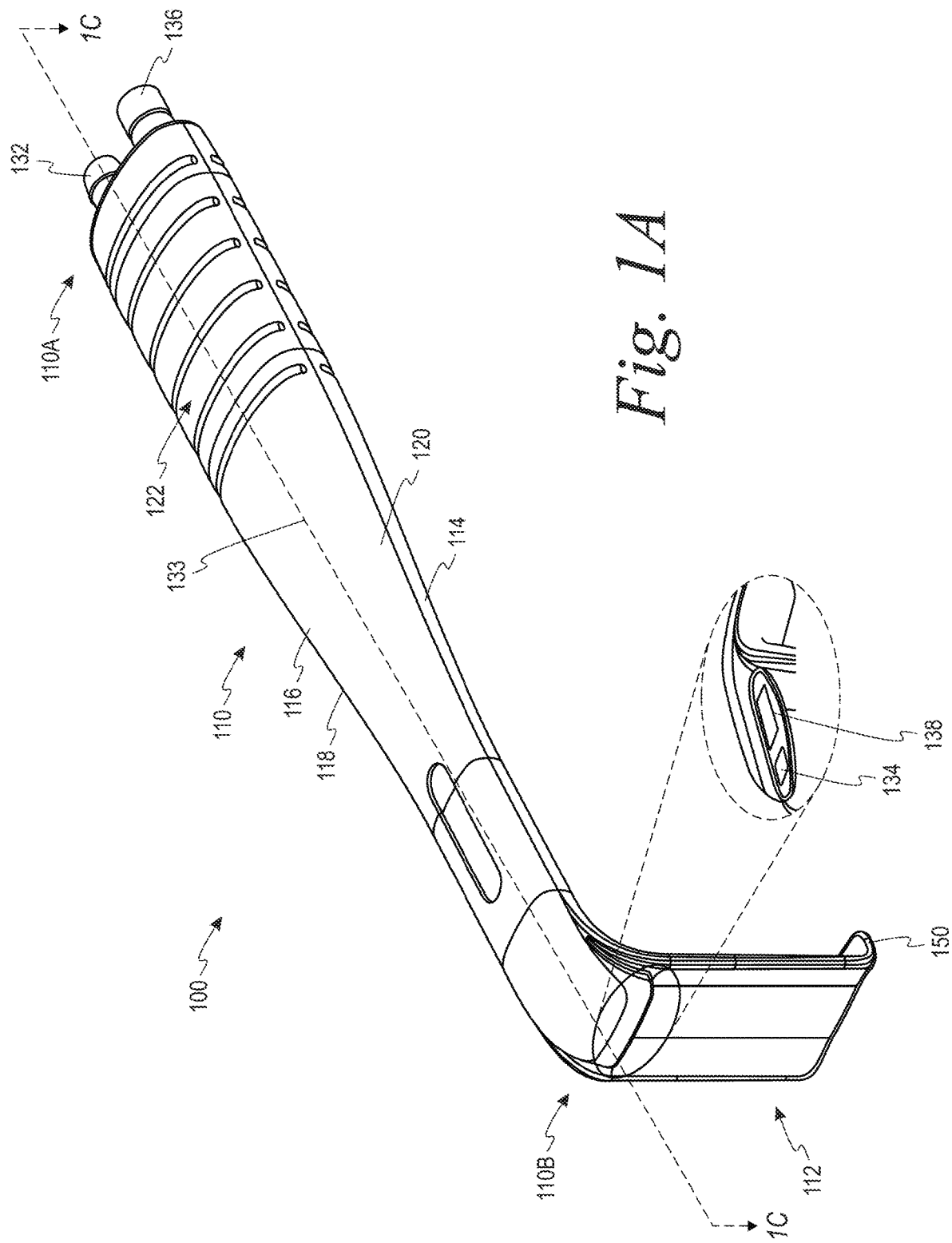
FIG. 1A depicts a perspective view of a surgical retractor, according to an example.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As noted above, a surgical retractor is a surgical instrument used to separate a surgical incision and/or retract tissue to provide access to underlying organs and/or tissue during a surgical procedure. As also noted above, the surgical retractor may include a handle that can be gripped by a medical practitioner and a retractor blade extending from the handle for engaging the tissue to be retracted. In some implementations, the surgical retractor may further include illumination features for illuminating the surgical site and/or suction features for evacuating substances (e.g., surgical smoke) from the surgical site while retracting the tissue.

One challenge associated with incorporating illumination features and/or suction features in the surgical retractor is that such features generally increase a size of the surgical retractor. For some types of surgical procedures, the increased size of the surgical retractor may impair a medical practitioner's ability to visualize the surgical site. For instance, the size of the surgical retractor may affect a medical practitioner's ability to visualize the surgical site during surgical procedures that involve a relatively small incision such as, for example, a lumpectomy procedure.

The present disclosure provides for surgical retractors that can address one or more of the challenges associated with incorporating illumination features and suction features in a surgical retractor. Within examples, a surgical retractor can include an elongated shaft that defines an internal chamber, and a retractor blade that extends from the elongated shaft. The elongated shaft can further include a suction conduit in a first lateral portion of the internal chamber and a light conduit in a second lateral portion of the internal chamber. An optical waveguide is in the light conduit. In this arrangement, the surgical retractor can apply suction to the surgical site via the suction conduit, and the surgical retractor can illuminate the surgical site via the optical waveguide in the light conduit while retracting tissue using the retractor blade. Because the suction conduit is in the first lateral portion of the internal chamber and the light conduit is in the second lateral portion of the internal chamber, the surgical retractor can have smaller height than other surgical retractors in which light features and suction features are vertically offset from each other or disposed in a stacked arrangement.

Also, in some examples, the retractor blade can include a proximal portion and a distal portion, and the proximal portion can be wider than the distal portion. As used herein, the term "proximal" is intended to mean closer to the elongated shaft, and the term "distal" is intended to mean farther from the elongated shaft. Making the proximal portion wider than the distal portion can help to accommodate a width of the surgical retractor at the suction conduit and the light conduit, while providing a relatively narrow retractor blade for engaging tissue in a relatively small incision.

Figure 1B:
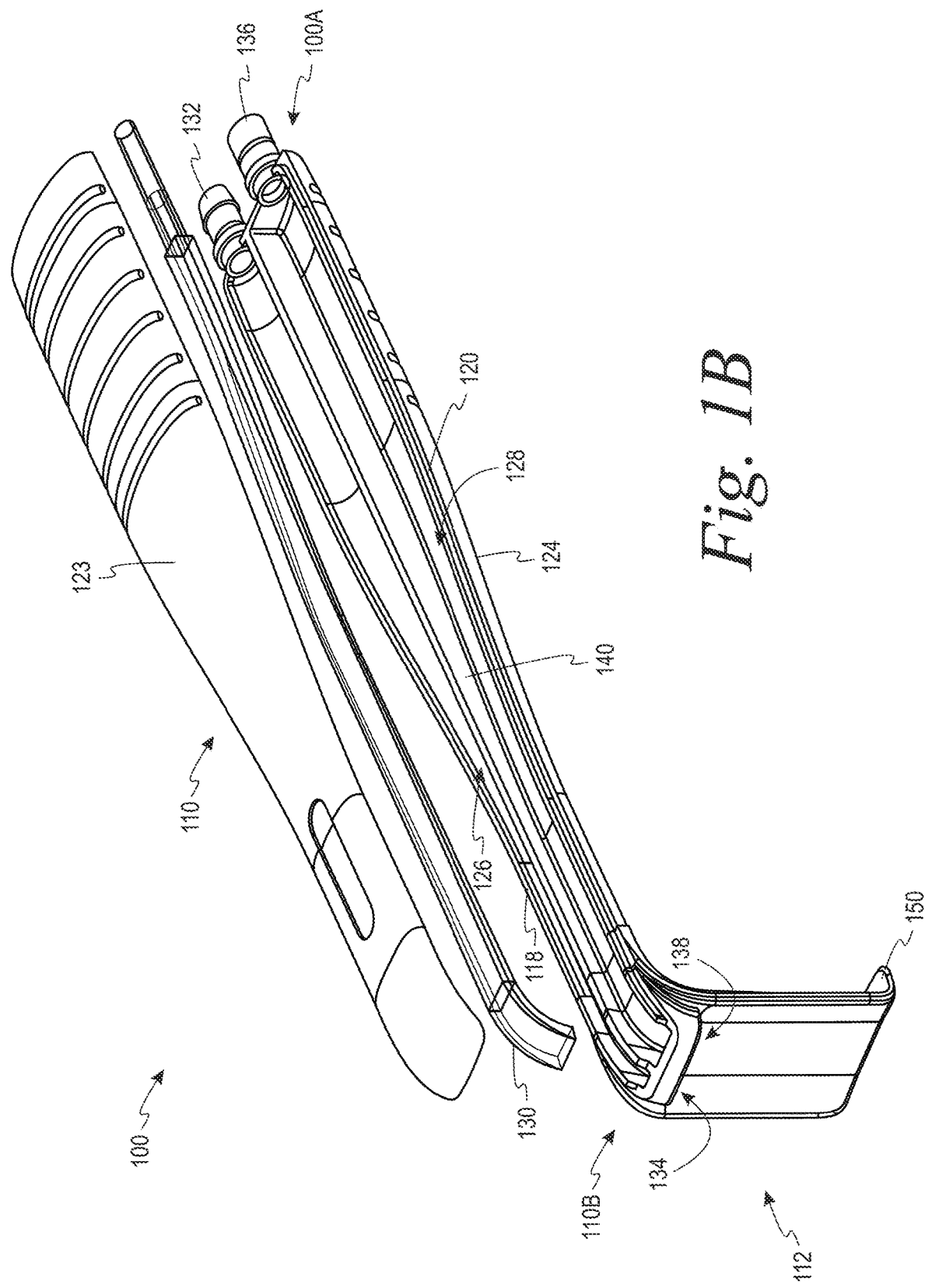
FIG. 1B depicts an exploded view of the surgical retractor shown in FIG. 1A, according to an example.
Figure 1C:
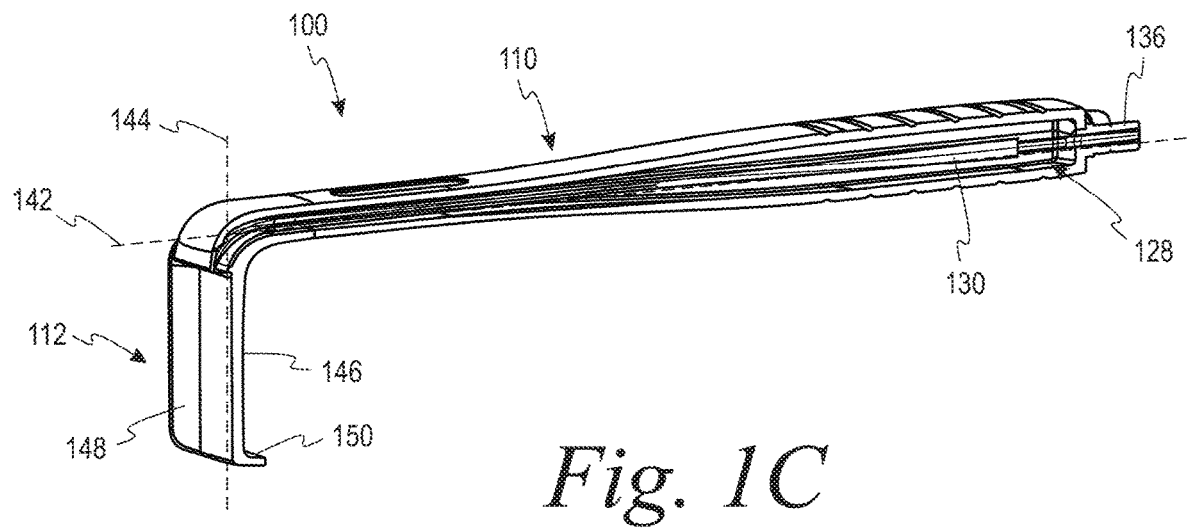
FIG. 1C depicts a cross-sectional view of the surgical retractor 100 of the surgical retractor shown in FIG. 1A, according to an example.
Figure 1D:
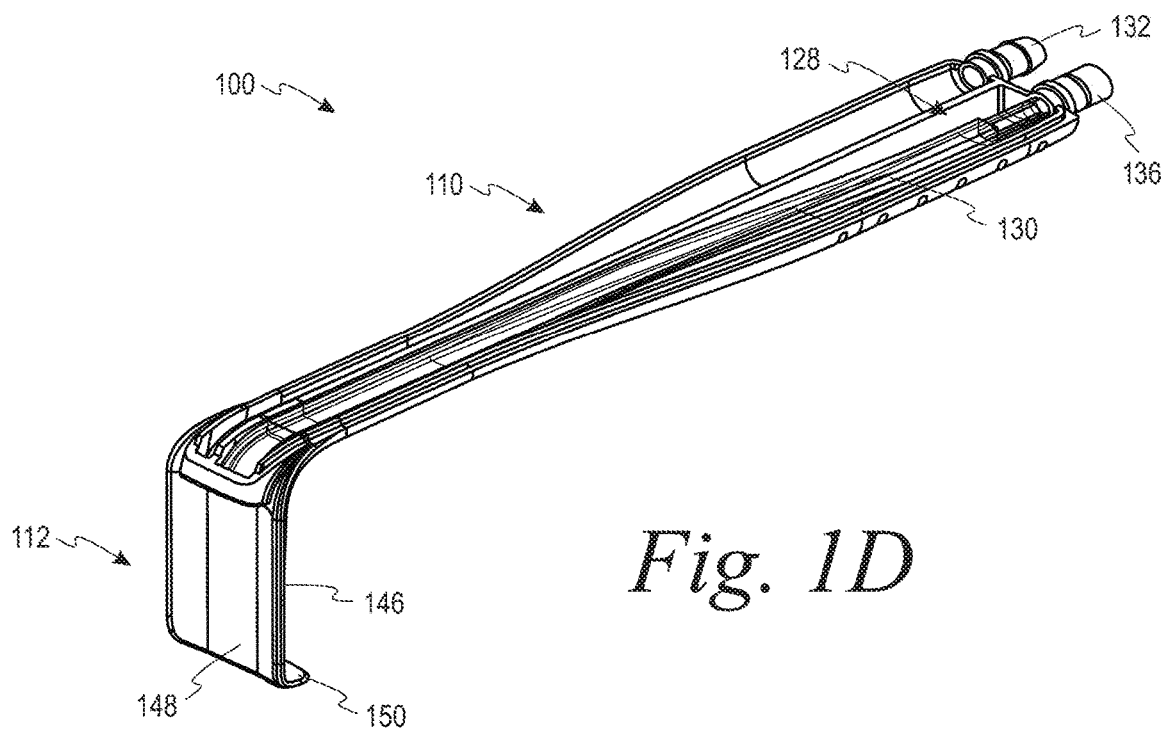
FIG. 1D depicts the surgical retractor of FIG. 1A with a cover portion removed, according to an example.
Figure 1E:
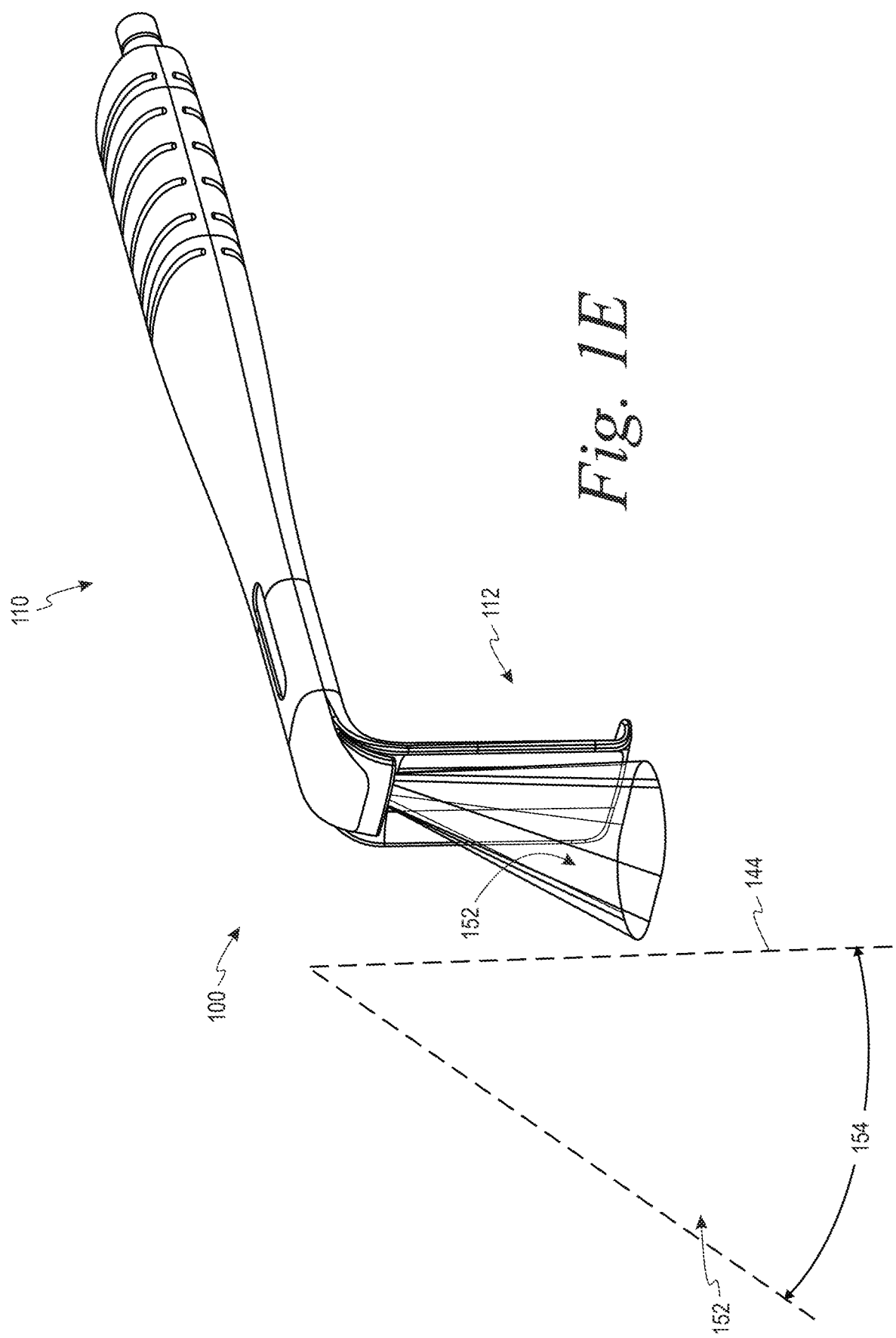
FIG. 1E depicts the surgical retractor of FIG. 1A emitting light, according to an example.

Referring now to FIGS. 1A-1E, a surgical retractor 100 is shown according to an example. In particular, FIG. 1A depicts a perspective view of the surgical retractor 100, FIG. 1B depicts an exploded view of the surgical retractor 100, FIG. 1C depicts a cross-sectional view of the surgical retractor 100, FIG. 1D depicts the surgical retractor 100 with a cover portion removed, and FIG. 1E depicts the surgical retractor 100 emitting light.

As shown in FIG. 1A, the surgical retractor 100 includes an elongated shaft 110 and a retractor blade 112. The elongated shaft 110 extends from a first end 110A to a second end 110B. In this example, the elongated shaft 110 includes a bottom surface 114, a top surface 116, a first lateral side 118, and a second lateral side 120. As used herein, the term "bottom surface" is intended to mean a surface that faces a patient's retracted tissue when the surgical retractor 100 retracts tissue, and the term "top surface" is intended to mean a surface that faces away from the patients' retracted tissue when the surgical retractor 100 retracts tissue.

Additionally, as shown in FIG. 1A, the elongated shaft 110 includes a handle portion 122 at the first end 110A of the elongated shaft 110. The handle portion 122 can be configured to facilitate gripping and/or manipulating the surgical retractor 100. For instance, the handle portion 122 can include at least one surface feature chosen from a plurality of grooves and a textured surface that helps a medical practitioner grip the surgical retractor 100.

The handle portion 122 can additionally or alternatively have cross-sectional dimensions and a shape that helps the medical practitioner grip and/or operate the surgical retractor 100. In some implementations, the cross-sectional dimensions and/or the shape of the handle portion 122 may be relatively large to facilitate gripping the surgical retractor 100, and the cross-sectional dimensions and/or the shape of the second end 110B of the elongated shaft 110 can be relatively small to mitigate impairing the medical practitioner's view of the surgical site. For instance, in FIG. 1A, the elongated shaft 110 has a width between the first lateral side 118 and the second lateral side 120 that tapers inwardly towards a center 133 of the elongated shaft 110 along a direction from the first end 110A toward the second end 110B. Additionally, for instance, the elongated shaft 110 can have a height between the top surface 116 and the bottom surface 114, and the height of the elongated shaft 110 can be greater at the handle portion 122 than the height of the elongated shaft 110 at the second end 110B.

As an example, the height of the elongated shaft 110 at the second end 110B can be a height between approximately 7 millimeters (mm) and approximately 11 mm. Additionally, as an example, the height of the handle portion 122 can be a height between approximately 15 millimeters (mm) and approximately 20 mm.

As shown in FIG. 1B, the elongated shaft 110 defines an internal chamber. For instance, in FIG. 1B, the elongated shaft 110 can be formed by a cover portion 123 that is coupled to a base portion 124 to define the internal chamber between the cover portion 123 and the base portion 124. As examples, the cover portion 123 can be coupled to the base portion 124 by at least one process chosen from ultrasonic welding, radiofrequency welding, laser welding, applying an adhesive, press-fit, and snapping fitting Additionally, the elongated shaft 110 includes a suction conduit 126 that can evacuate substances (e.g., surgical smoke) from the surgical site and a light conduit 128 that can house an optical waveguide 130 for illuminating the surgical site while surgical retractor 100 retracts tissue. As shown in FIG. 1B, the elongated shaft 110 includes the suction conduit 126 in a first lateral portion of the internal chamber adjacent to the first lateral side 118, and the light conduit 128 in a second lateral portion of the internal chamber adjacent to the second lateral side 120. The suction conduit 126 extends from a suction port 132 at the first end 110A to a suction aperture 134 at the second end 110B. The light conduit 128 extends from a light-input port 136 at the first end 110A to a light aperture 138 at the second end 110B. In FIG. 1B, the suction conduit 126 and the light conduit 128 are substantially coplanar between the first end 110A and the second end 110B. As such, the suction conduit 126 and the light conduit 128 are in a side-by-side arrangement, and the suction conduit 126 and the light conduit 128 can have a common height at each point in space along the elongated shaft 110. This can help to reduce (or minimize) a height between the bottom surface 114 and the top surface 116 at the second end 110B and, thus, improve (or maximize) visibility of the surgical site while retracting tissue using the surgical retractor 100.

In FIGS. 1B-1D, the suction conduit 126 and the light conduit 128 are coplanar and have a common height at each point in space along the elongated shaft 110. This can help to enhance or maximize the respective sizes of the suction conduit 126 and the light conduit 128 in the elongated shaft 110. In another example, the suction conduit 126 and the light conduit 128 can have different heights so long as a center axis of the suction conduit 126 and a center axis of the light conduit 128 are coplanar in a plane through or parallel to the width of the elongated shaft 110.

Additionally, in FIGS. 1A-1D, the light aperture 134 has a width that is different than a width of the suction aperture 138. In particular, in FIGS. 1A-1D, the width of the light aperture 134 is greater than the width of the suction aperture 138. This arrangement can help to provide greater illumination than an arrangement in which the width of the light aperture 134 is equal to or less than the width of the suction aperture 138. However, in other examples, the width of the light aperture 134 can be less than or equal to the width of the suction aperture 138 to enhance the suction capabilities of the surgical retractor 100.

Within examples, the suction conduit 126 is configured to apply a vacuum to the suction aperture 134 when the suction port 132 is coupled to a vacuum source. For instance, the suction conduit 126 can be fluidly sealed between the suction port 132 and the suction aperture 134. This can help to efficiently apply suction at the suction aperture 134 and transport substances received in the suction aperture 134 along the suction conduit 126 to the suction port 132 so that the substances can be removed away from the surgical site via the surgical retractor 100.

The suction conduit 126 can additionally or alternatively be fluidly sealed from the light conduit 128. This can help to mitigate (or prevent) substances transported through the suction conduit 126 from collecting on the optical waveguide 130, which may negatively affect optical transmission of light using the optical waveguide 130. In FIG. 1B, the base portion 124 includes a partition wall 140 that separates the suction conduit 126 and the light conduit 128 from each other. The partition wall 140 can have a height such that the partition wall 140 engages the cover portion 123 when the cover portion 123 is coupled to the base portion 124. In another example, the cover can additionally or alternatively include the partition wall 140.

As shown in FIGS. 1C-1D, the optical waveguide 130 is in the light conduit 128 of the elongated shaft 110. The optical waveguide 130 can be a non-fiber optic waveguide. For example, the optical waveguide 130 can be formed from a material chosen from a cyclic olefin copolymer, a cyclic olefin polymer, acrylic, and TPX polymethylpentene. As shown in FIGS. 1C-1D, the optical waveguide 130 can extend into the light-input port 136. The light-input port 136 is configured to couple a light source to the optical waveguide 130 in the light conduit 128. As examples, the light source can include a fiber optic cable, a light-emitting diode (LED), an organic light emitting diode (OLED), and/or a laser light source. In one example, the light-input port 136 can be a fiber optic cable connector such as, for instance, an Adapter Cable Medical Instruments (ACMI) connector.

As described above, in some examples, the elongated shaft 110 can have a height between the top surface 116 and the bottom surface 114, and the height of the elongated shaft 110 can be greater at the handle portion 122 than the height of the elongated shaft 110 at the second end 110B. With the reduced height of the elongated shaft 110 at the second end 110B, a size of the light conduit 128 in the elongated shaft 110 may also reduce between the first end 110A and the second end 110B. Within examples, the optical waveguide 130 can have a cross-sectional area that varies over a length of the elongated shaft 110 between the first end 110A and the second end 110B.

For example, it may be beneficial for the optical waveguide 130 to have a relatively large cross-sectional area at the first end 110A and a relatively smaller cross-sectional area at the second end 110B to facilitate reducing the height of the elongated shaft 110 at the second end 110B and thereby reducing visual impairment of the surgical site. However, reducing the cross-sectional area of the optical waveguide 130 between the first end 110A and the second end 110B may have the effect of increasing an output beam angle of the light in the optical waveguide 130. This in turn has the potential to cause glare for the medical practitioner using the surgical retractor 100.

Figure 2A:
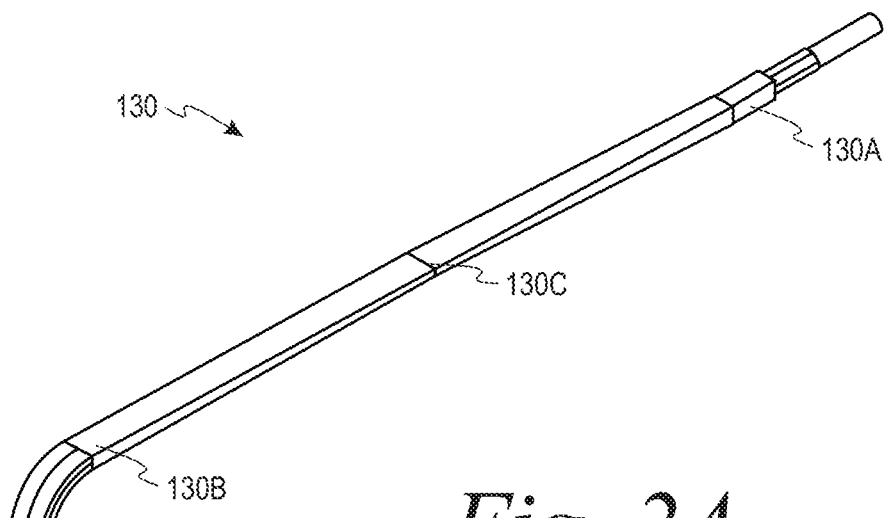
FIG. 2A depicts a perspective view of an optical waveguide, according to an example.
Figure 2B:
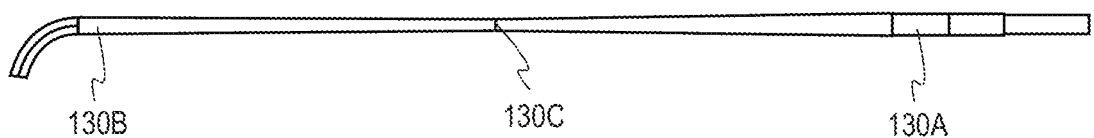
FIG. 2B depicts a side view of the optical waveguide shown in FIG. 2A, according to an example.

FIG. 2A depicts a perspective view of the optical waveguide 130, and FIGS. 1C and 2 depict a side view of the optical waveguide 130. The optical waveguide 130 can extend from a first-waveguide end 130A to a second-waveguide end 130B. The optical waveguide 130 can have a first cross-sectional area at the first-waveguide end 130A, the optical waveguide 130 can have a second cross-sectional area at the second-waveguide end 130B, and the optical waveguide 130 can have a third cross-sectional area at an intermediate point 130C between the first-waveguide end 130A and the second-waveguide end 130B. In one implementation, the intermediate point 130C can be a midpoint between the first-waveguide end 130A and the second-waveguide end 130B. The third cross-sectional area is less than the first cross-sectional area and the second cross-sectional area. This reduction in cross-sectional area at the intermediate point 130C can cause relatively wide angle light rays to leak out of the optical waveguide 130 such that only relatively narrow angle light rays will continue to propagate through the optical waveguide 130. As such, a beam angle at the second-waveguide end 130B is reduced, which can help to reduce glare.

As an example, FIG. 1E depicts the surgical retractor 100 with light 152 exiting the optical waveguide 130 at a light beam angle 154. The light beam angle 154 can be an angle between the longitudinal axis 144 of the retractor blade 112 and an axis 156 of a light ray (from emitted from the optical waveguide 130) that is farthest from the longitudinal axis 144 of the retractor blade 112. In one example, the light beam angle 154 can be an angle between approximately 0 degrees and approximately 60 degrees. In another example, the light beam angle 154 can be approximately 60 degrees. In another example, the light beam angle 154 can be approximately 52 degrees.

Referring back to FIGS. 2A-2B, in some implementations, the third cross-sectional area of the optical waveguide 130 at the intermediate point 130C can be approximately half the first cross-sectional area at the first-waveguide end 130A. This can cause the light beam angle to increase by a factor of approximately 1.4 (i.e., the square root of 2), which can cause the widest angle light rays to exceed the critical angle of the optical waveguide 130 and leak out of the optical waveguide 130. The critical angle of the optical waveguide 130 is the smallest angle of incidence that yields total reflection. The relatively small angle light rays (e.g., the light rays having an angle less than the critical angle) continue to propagate through the increasing cross-sectional area of the optical waveguide 130 between the intermediate point 130C and the second-waveguide end 130B. Since the wide angle rays are no longer present, the light output from the light aperture 138 as a relatively narrow beam of light.

The relatively narrow beam of light can be achieved based on a preservation of etendue in accordance with the following equation:

$$G = pi * A * NA^2 \quad \text{(equation 1)}$$

where G is etendue, A is cross sectional area of the optical waveguide 130, and NA is the numerical aperture. NA is related to the light beam angle at any given cross section by NA=sin (alpha), where alpha is the light beam angle. Etendue remains constant throughout the optical waveguide 130.

Conventionally, optical waveguides generally have constant cross sectional areas between the first-waveguide end and the second-waveguide end so that etendue is preserved, there is no resulting increase in light beam angle, and no light leaks out. By contrast, in FIGS. 2A-2B, the cross sectional area of the optical waveguide 130 is reduced by half at the intermediate point 130C, causing a resulting change in the light beam angle.

In an example, a light beam angle at the first-waveguide end 130A can be approximately 33 degrees and a critical angle of the optical waveguide 130 can be approximately 41 degrees. By reducing the cross-sectional area of the optical waveguide 130 by half at the intermediate point 130C, the light beam angle increases from approximately 33 degrees to approximately 51 degrees. Because the light beam angle of approximately 51 degrees is greater than the critical angle of approximately 41 degrees at the intermediate point 130C, some rays of light will permanently leak out of the optical waveguide 130 at the intermediate point 130C. By increasing the cross-sectional area of the optical waveguide 130 between the intermediate point 130C and the second-waveguide end 130B, the narrower light rays will remain.

In the example described above, the third cross-sectional area of the optical waveguide 130 at the intermediate point 130C is approximately half the second cross-sectional area at the second-waveguide end 130B. However, in another example, the third cross-sectional area of the optical waveguide 130 at the intermediate point 130C can be approximately 40 percent to approximately 80 percent of the second cross-sectional area at the second-waveguide end 130B. In yet another example, the third cross-sectional area of the optical waveguide 130 at the intermediate point 130C can be approximately 40 percent to approximately 60 percent of the second cross-sectional area at the second-waveguide end 130B.

As one example, the first cross-sectional area at the first-waveguide end 130A can be approximately 4.25 millimeters (mm) in width by approximately 4.25 mm in height, the second cross-sectional area at the second-waveguide end 130B in width can be approximately 6.5 mm by approximately 2.7 mm in height, and the third cross-sectional area at the intermediate point 130C can be approximately 6.5 mm in width by approximately 1.35 mm in height.

As described above, the elongated shaft 110 can have a width between the first lateral side 118 and the second lateral side 120 that tapers inwardly towards the center 133 of the elongated shaft 110 along a direction from the first end 110A toward the second end 110B. As shown in FIG. 1B, the light conduit 128 can also narrow and/or taper towards the center 133 along the direction from the first end 110A toward the second end 110B. As a result, the light conduit 128 may have a non-linear shape. As shown in FIGS. 2A, a center axis of the optical waveguide 130 can be non-linear such that the first-waveguide end 130A of the optical waveguide 130 is laterally offset relative to the second-waveguide end 130B of the optical waveguide 130. This can help to accommodate the suction port 132 and the light-input port 136 within a relatively small amount of space at the first end 110A of the elongated shaft 110.

Referring to FIGS. 1A-1D, the elongated shaft 110 bends towards the retractor blade 112 at the second end 110B of the elongated shaft 110 such that the suction aperture 134 and the light aperture 138 face a surgical site when the retractor blade 112 retracts tissue. Similarly, the optical waveguide 130 can include a bend at the second end 110B such that the optical waveguide 130 faces the surgical site when the retractor blade 112 retracts tissue. This can help to direct light from the optical waveguide 130 toward the surgical site. As shown in FIGS. 1A-1D, the suction aperture 134 and the light aperture 138 can be coplanar. This can help to provide unimpaired access to the surgical site for both the suction aperture 134 and the light aperture 138.

As described above, the retractor blade 112 extends from the second end 110B of the elongated shaft 110. Within examples, a longitudinal axis 142 of the elongated shaft 110 can be at a non-zero angle relative to a longitudinal axis 144 of the retractor blade 112 (as shown in FIG. 1C). For instance, the angle between the longitudinal axis 142 of the elongated shaft 110 and the longitudinal axis 144 of the retractor blade 112 can be between approximately 45 degrees and approximately 135 degrees. In another example, the angle between the longitudinal axis 142 of the elongated shaft 110 and the longitudinal axis 144 of the retractor blade 112 can be approximately 90 degrees.

As shown in FIGS. 1C-1D, the retractor blade 112 can include a back surface 146 that faces the retracted tissue and a front surface 148 that faces away from the reacted tissue when the retractor blade 112 is retracting the tissue. As shown in FIG. 1D, the front surface 148 can have a concave shape. This can help to provide access to the surgical site with reduced (or minimal) stress on the retracted tissue and/or enhance the strength of the retractor blade 112.

The back surface 146 of the retractor blade 112 can include a protrusion 150, which extends in a direction that is parallel to a direction from the second end 110B of the elongated shaft 110 toward the first end 110A of the elongated shaft 110, such that the elongated shaft 110 and the retractor blade 112 define a hook shape. This can help to engage the retractor blade 112 with the tissue and hold back the tissue.

In FIGS. 1A-1E, the retractor blade 112 has a width that is substantially constant between a proximal portion of the retractor blade 112 and a distal portion of the retractor blade 112. In an example, the width of the retractor blade 112 can be a width between approximately 24 mm and approximately 28 mm. In another example, the width of the retractor blade 112 can be approximately 20 mm. This width may be beneficial for certain types of small incision procedures such as, for example, a lumpectomy procedure.

However, in other examples, the proximal portion of the retractor blade 112 can be wider than the distal portion of the retractor blade 112. This can help to accommodate a width of the surgical retractor 100 at the suction conduit 126 and the light conduit 128, while providing a relatively narrow retractor blade 112 for engaging tissue in a relatively small incision.

Figure 3A:
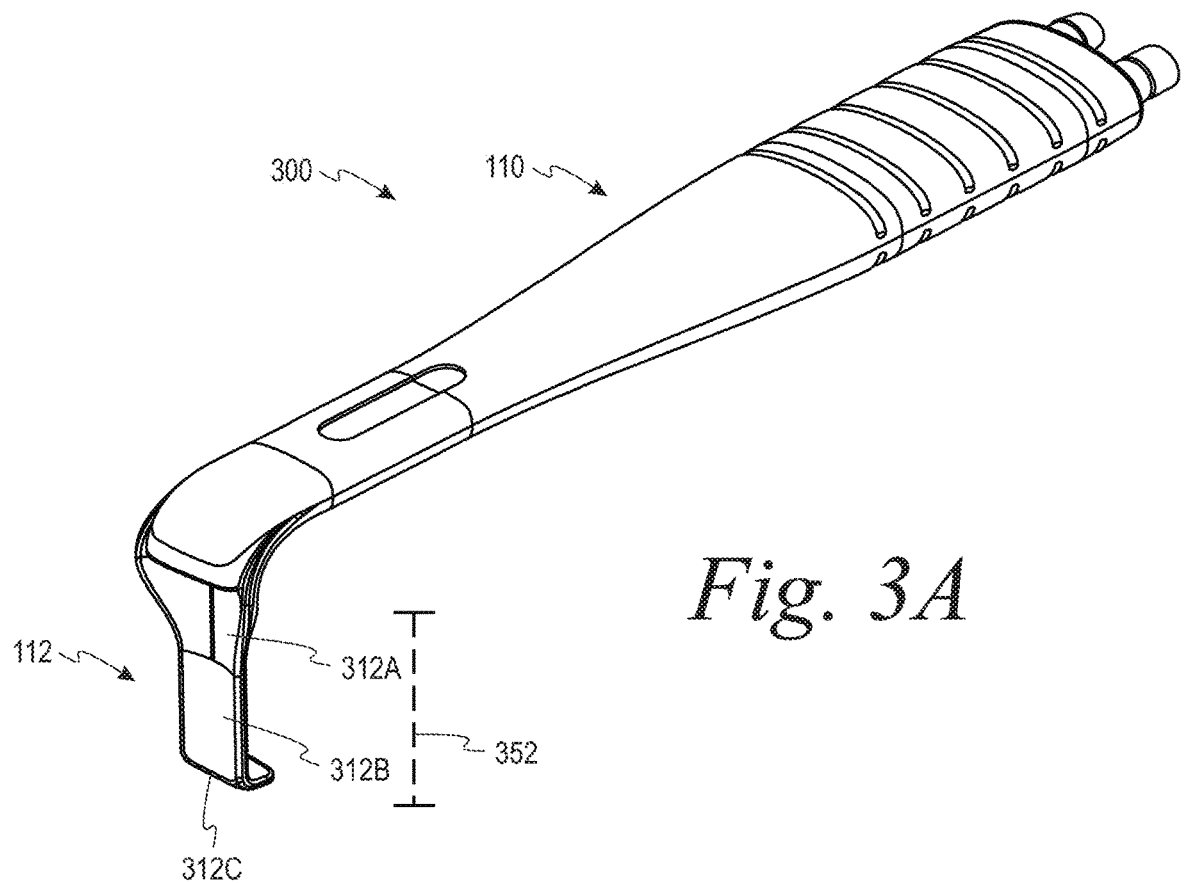
FIG. 3A depicts a first view of a surgical retractor, according to another example.
Figure 3B:
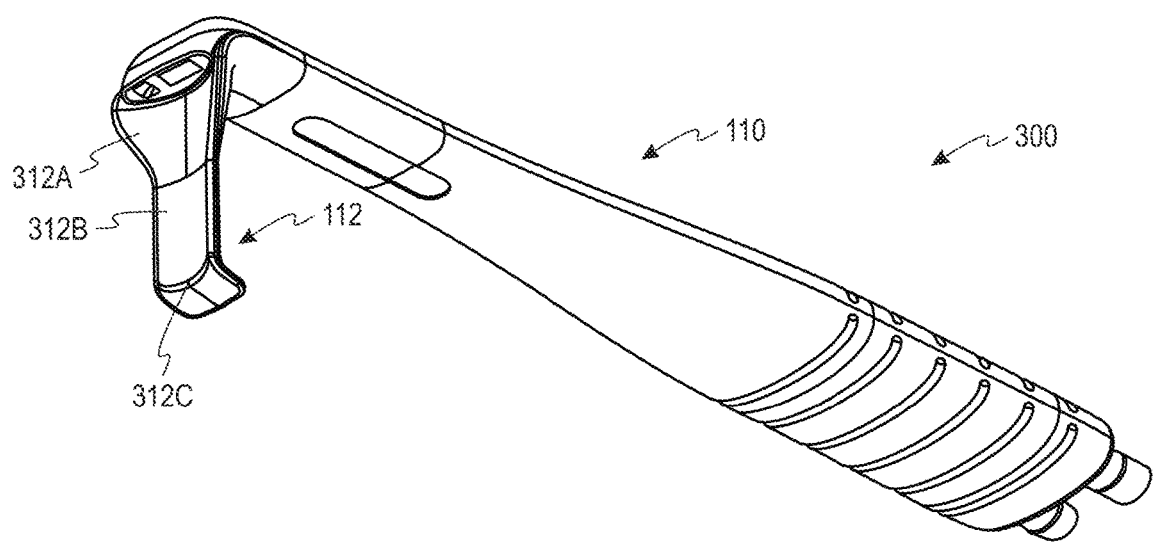
FIG. 3B depicts a second view of the surgical retractor shown in FIG. 3A, according to an example.

FIGS. 3A-3B depict a surgical retractor 300 according to another example. The surgical retractor 300 is substantially similar or identical to the surgical retractor 100 described above, except a proximal portion 312A of the retractor blade 112 is wider than a distal portion 312B of the retractor blade 112. For example, in FIGS. 3A-3B, the proximal portion 312A of the retractor blade 112 has a shape that tapers inwardly along a direction from the elongated shaft 110 toward the distal portion 312B of the retractor blade 112.

Additionally, the retractor blade 112 can have a length 352 in a dimension between the elongated shaft 110 and a distal-most end 312C of the retractor blade 112. In one example, the proximal portion 312A of the retractor blade 112 includes at least 10 percent of the length 352 of the retractor blade 112 and the distal portion 312B of the retractor blade 112 can extend for a remainder of the length 352 of the retractor blade 112. In another example, the proximal portion 312A of the retractor blade 112 includes approximately 20 percent to approximately 50 percent of the length 352 of the retractor blade 112 and the distal portion 312B of the retractor blade 112 can extend for a remainder of the length 352 of the retractor blade 112. In this way, the relatively large width of the proximal portion 312A can help to enhance the rigidity and strength of the retractor blade 112 while the smaller width of the distal portion 312B of the retractor blade 112 can help to retract tissue at a relatively small incision.

In an example, the width of the proximal portion 312A of the retractor blade 112 can be a width between approximately 20 mm and approximately 24 mm and the width of the distal portion 312B of the retractor blade 112 can be a width between approximately 8 mm and approximately 12 mm.

Within examples, the retractor blade 112 of the surgical retractor 100 shown in FIGS. 1A-1E and/or the surgical retractor 300 shown in FIGS. 3A-3B can have a length 352 between approximately 30 mm and approximately 50 mm. In some examples, a plurality of the surgical retractors 100, 300 can be provided as a kit in which the retractor blade 112 of each surgical retractor 100, 300 has a different length and/or width. In one implementation, the kit can include at least two surgical retractors chosen from (i) a first surgical retractor 100 having the retractor blade 112 with a length 352 of approximately 30 mm and a width of approximately 24 mm, (ii) a second surgical retractor 100 having the retractor blade 112 with a length 352 of approximately 50 mm and a width of approximately 24 mm, (iii) a third surgical retractor 300 having the retractor blade 112 with a length 352 of approximately 30 mm and a width of approximately 12 mm, and (iv) a fourth surgical retractor 100, 300 having the retractor blade 112 with a length 352 of approximately 50 mm and a width of approximately 12 mm.

In some examples, the surgical retractors 100, 300 shown in FIGS. 1A-3B can be single-use, disposable surgical retractors 100, 300. Also, within examples, the surgical retractors 100, 300 can be sterilized and packaged in a packaging material that maintains the sterility of the surgical retractors 100, 300 prior to use.

Figure 4:
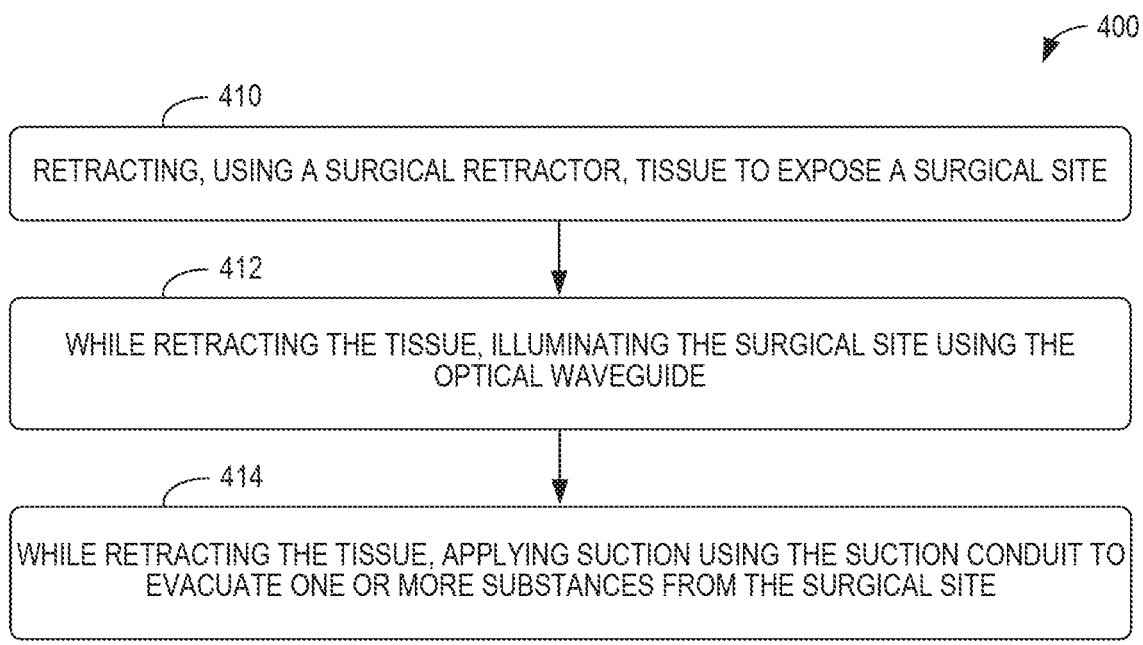
FIG. 4 depicts a flowchart for a method of retracting tissue, according to an example.

Referring now to FIG. 4, a flowchart for a process 400 of retracting tissue is shown according to an example. At block 410, the process 400 can include retracting, using a surgical retractor, tissue to expose a surgical site. The surgical retractor includes an elongated shaft extending from a first end to a second end, and a retractor blade extending from the second end of the elongated shaft. The elongated shaft defines an internal chamber. The elongated shaft includes a handle portion at the first end of the elongated shaft, a suction conduit in a first lateral portion of the internal chamber, and a light conduit in a second lateral portion of the internal chamber. The suction conduit extends from a suction port at the first end to a suction aperture at the second end. The light conduit extends from a light-input port at the first end to a light aperture at the second end. The suction conduit and the light conduit can be substantially coplanar between the first end and the second end. The surgical retractor also includes an optical waveguide in the light conduit of the elongated shaft.

At block 412, the process 400 can include, while retracting the tissue, illuminating the surgical site using the optical waveguide. At block 414, the process 400 can further include, while retracting the tissue, applying suction using the suction conduit to evacuate one or more substances from the surgical site.

Figure 5:
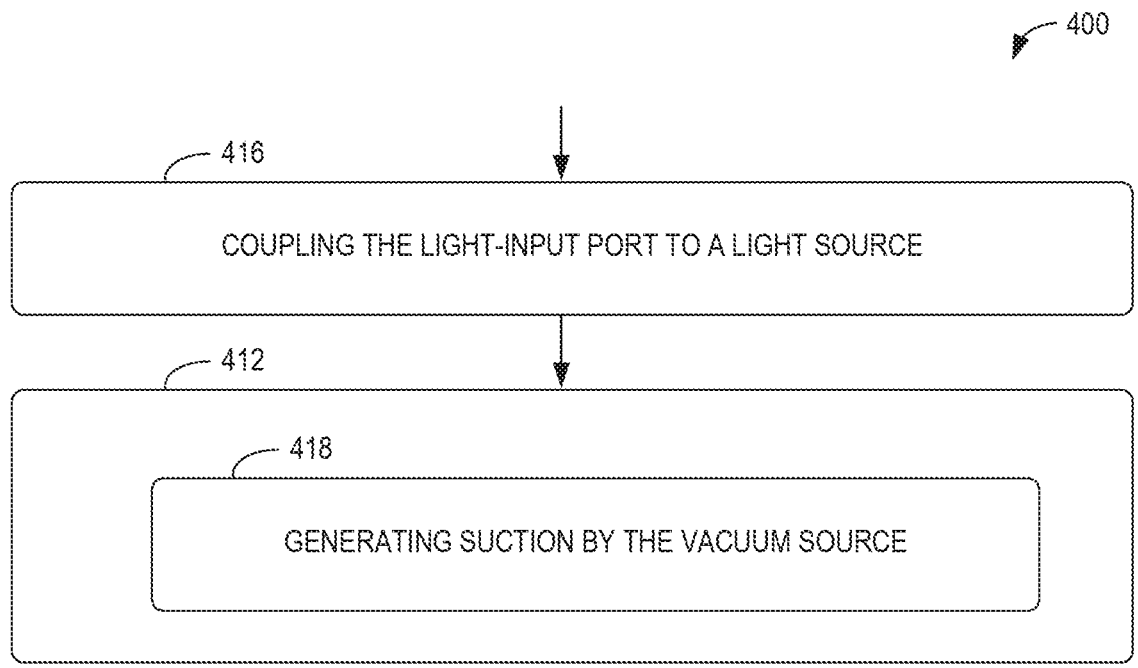
FIG. 5 depicts a flowchart for a method retracting tissue that can be used with the method shown in FIG. 4, according to an example.

FIGS. 5-8 depict additional aspects of the process 400 according to further examples. As shown in FIG. 5, the process 400 can also include coupling the light-input port to a light source at block 416. Also, in FIG. 5, illuminating the surgical site at block 412 can include transmitting, via the light-input port, light from the light source to the optical waveguide in the light conduit at block 418.

Figure 6:
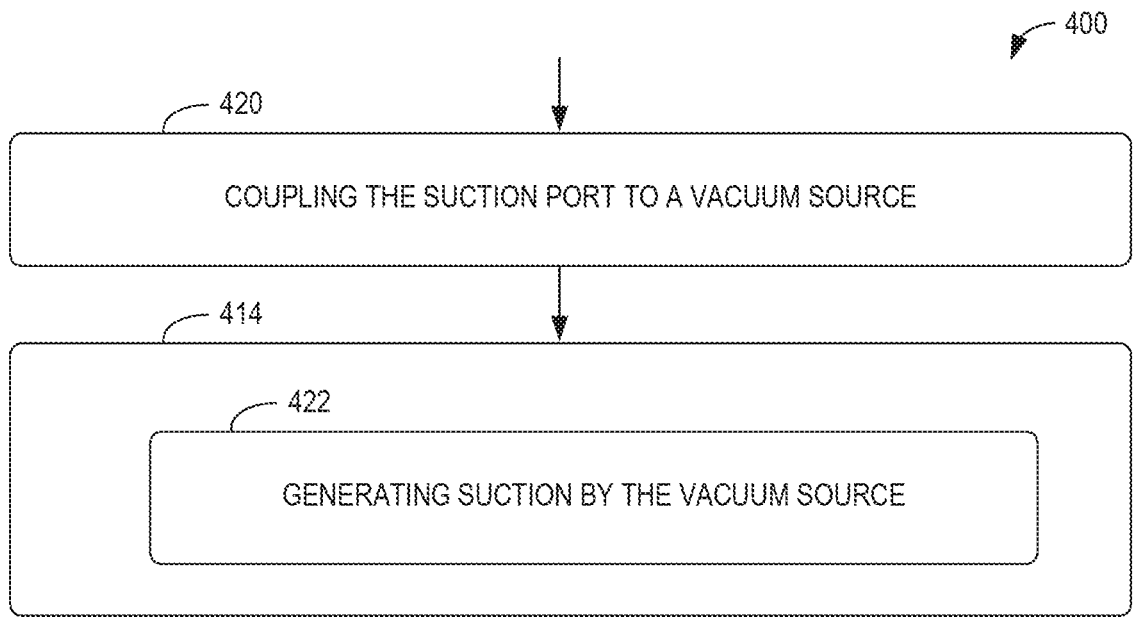
FIG. 6 depicts a flowchart for a method retracting tissue that can be used with the method shown in FIG. 4, according to an example.

As shown in FIG. 6, the process 400 can further include coupling the suction port to a vacuum source at block 420. Also, in FIG. 6, applying suction using the suction conduit at block 414 can include generating suction by the vacuum source at block 422.

Figure 7:
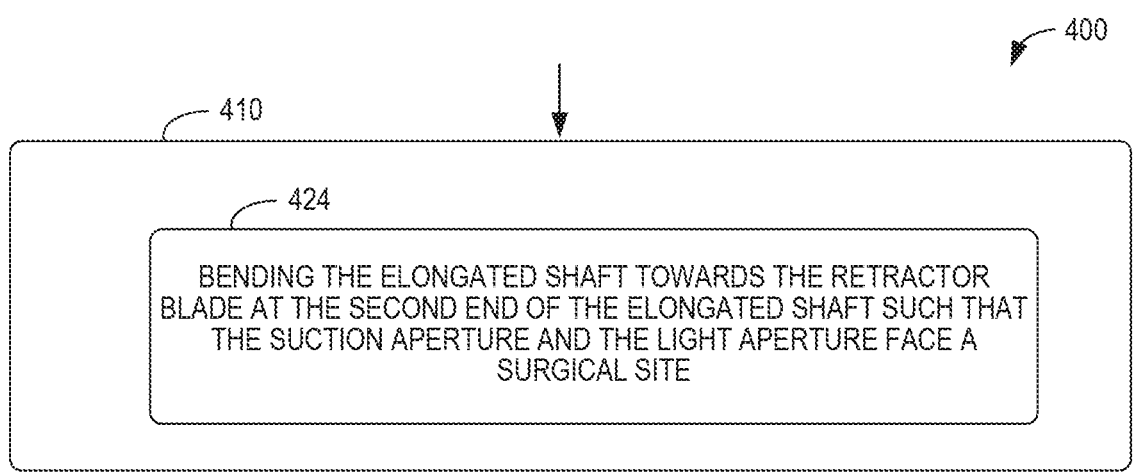
FIG. 7 depicts a flowchart for a method retracting tissue that can be used with the method shown in FIG. 4, according to an example.

As shown in FIG. 7, retracting the tissue at block 410 can include bending the elongated shaft towards the retractor blade at the second end of the elongated shaft such that the suction aperture and the light aperture face a surgical site at block 424.

Figure 8:
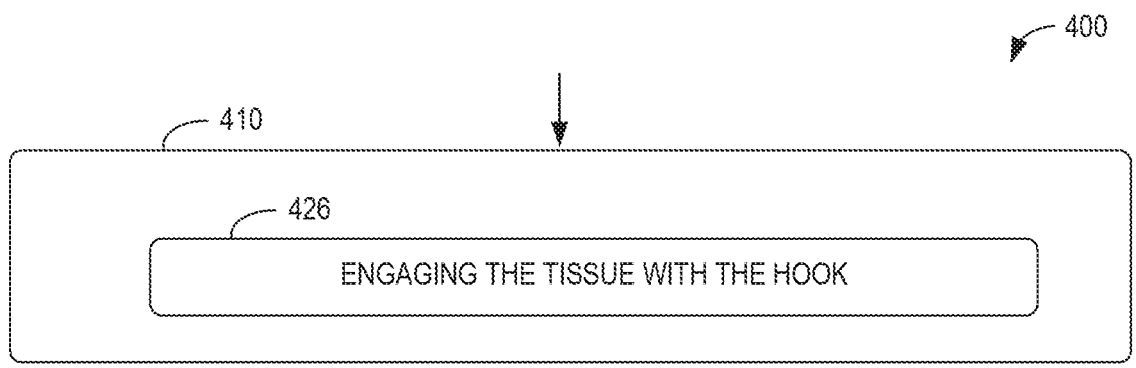
FIG. 8 depicts a flowchart for a method retracting tissue that can be used with the method shown in FIG. 4, according to an example.

In FIG. 8, the retractor blade can include a protrusion, which extends in a direction that is parallel to a direction from the second end of the elongated shaft toward the first end of the elongated shaft, such that the elongated shaft and the retractor blade define a hook shape. As shown in FIG. 8, retracting the tissue at block 410 can include engaging the tissue with the hook at block 426.

Figure 9:
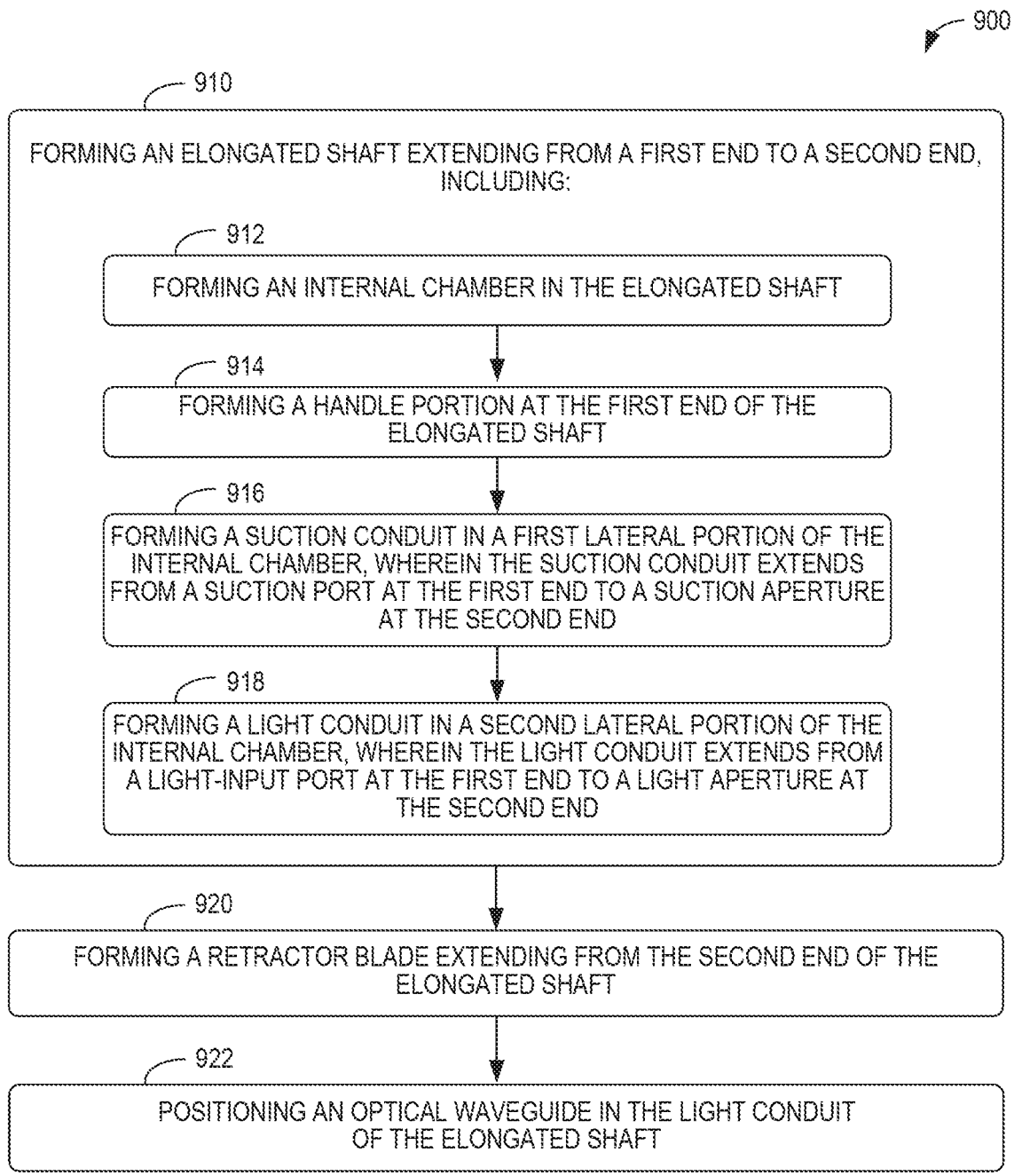
FIG. 9 depicts a flowchart for a method of making a surgical retractor, according to an example.

Referring now to FIG. 9, a flowchart for a process 900 of making a surgical retractor is shown according to an example. At block 910, the process 900 includes forming an elongated shaft extending from a first end to a second end. As shown in FIG. 9, forming the elongated shaft at block 910 can include: (i) forming an internal chamber in the elongated shaft at block 912, (ii) forming a handle portion at the first end of the elongated shaft at block 914, (iii) forming a suction conduit in a first lateral portion of the internal chamber, wherein the suction conduit extends from a suction port at the first end to a suction aperture at the second end at block 916, and (iv) forming a light conduit in a second lateral portion of the internal chamber, wherein the light conduit extends from a light-input port at the first end to a light aperture at the second end at block 918.

Additionally, as shown in FIG. 9, the process 900 includes forming a retractor blade extending from the second end of the elongated shaft at block 920. The process 900 also includes positioning an optical waveguide in the light conduit of the elongated shaft at block 922.

Figure 10:
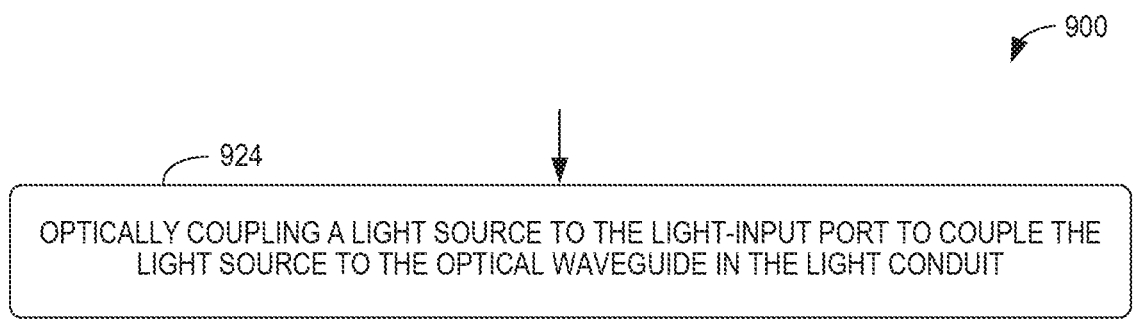
FIG. 10 depicts a flowchart for a method retracting tissue that can be used with the method shown in FIG. 9, according to an example.

FIGS. 10-20 depict additional aspects of the process 900 according to further examples. As shown in FIG. 10, the process 900 can also include optically coupling a light source to the light-input port to couple the light source to the optical waveguide in the light conduit at block 924.

Figure 11:
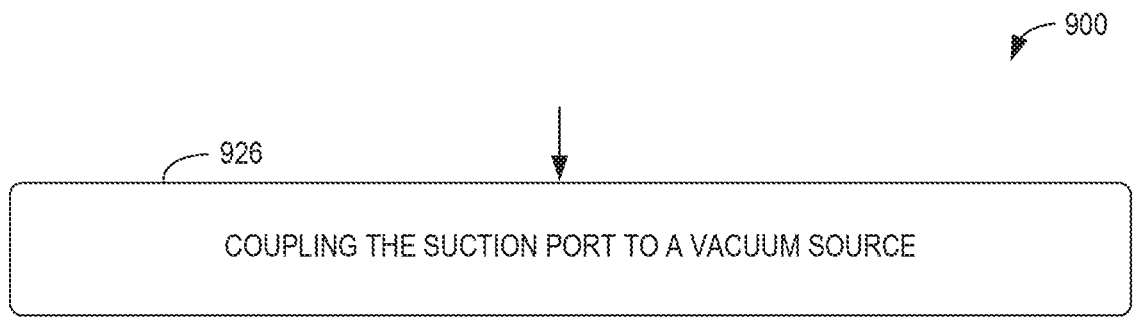
FIG. 11 depicts a flowchart for a method retracting tissue that can be used with the method shown in FIG. 9, according to an example.

As shown in FIG. 11, the process 900 can further include coupling the suction port to a vacuum source at block 926.

Figure 12:
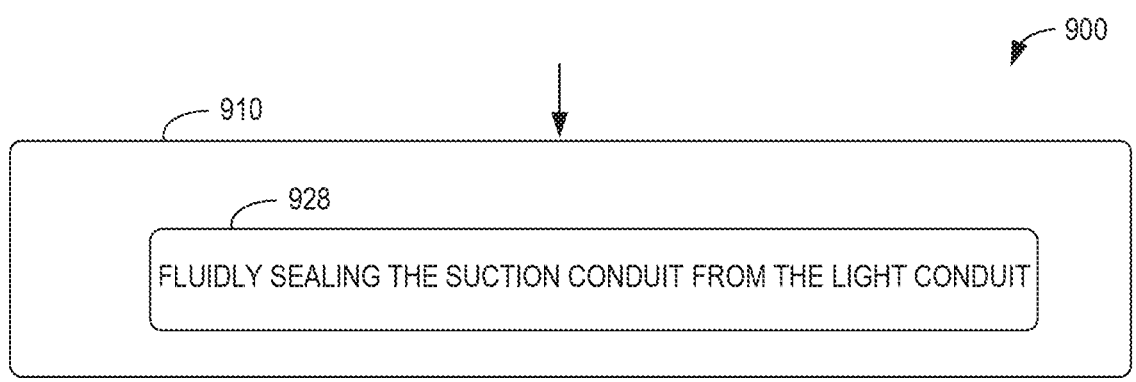
FIG. 12 depicts a flowchart for a method retracting tissue that can be used with the method shown in FIG. 9, according to an example.

As shown in FIG. 12, forming the elongated shaft at block 910 can further include fluidly sealing the suction conduit from the light conduit at block 928.

Figure 13:
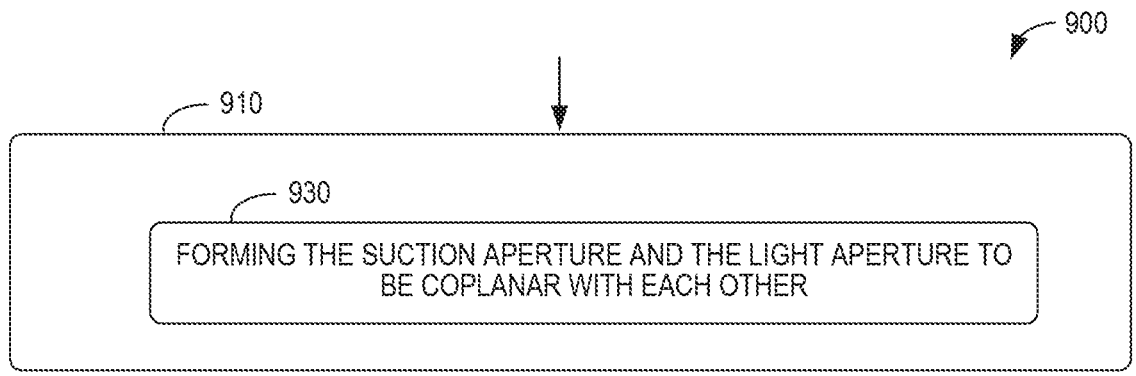
FIG. 13 depicts a flowchart for a method retracting tissue that can be used with the method shown in FIG. 9, according to an example.

As shown in FIG. 13, forming the elongated shaft at block 910 can further include forming the suction aperture and the light aperture to be coplanar with each other at block 930.

Figure 14:
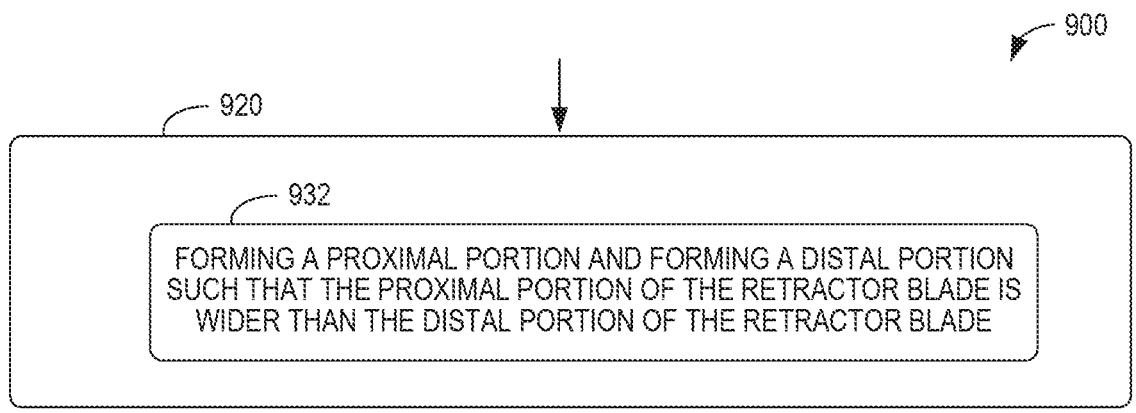
FIG. 14 depicts a flowchart for a method retracting tissue that can be used with the method shown in FIG. 9, according to an example.

As shown in FIG. 14, forming the retractor blade at block 920 can include forming a proximal portion and forming a distal portion such that the proximal portion of the retractor blade is wider than the distal portion of the retractor blade at block 932.

Figure 15:
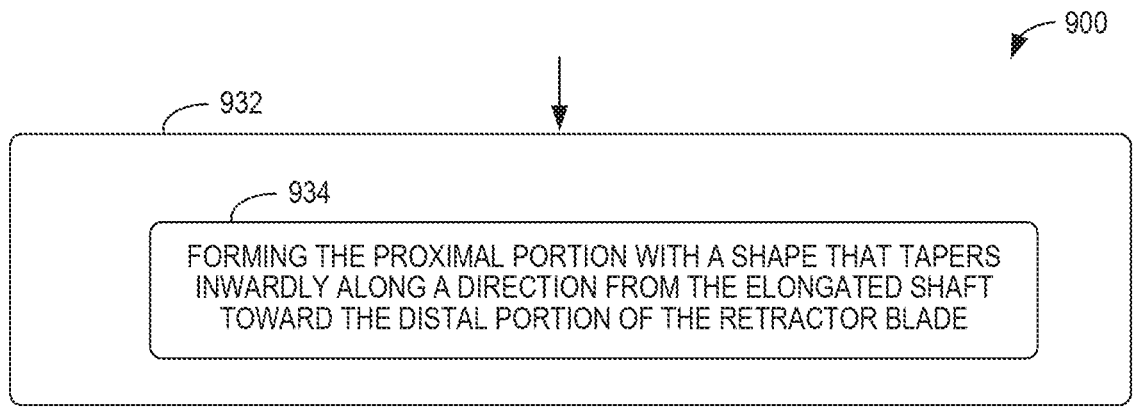
FIG. 15 depicts a flowchart for a method retracting tissue that can be used with the method shown in FIG. 14, according to an example.

As shown in FIG. 15, forming the proximal portion of the retractor blade at block 932 can include forming the proximal portion with a shape that tapers inwardly along a direction from the elongated shaft toward the distal portion of the retractor blade at block 934.

Figure 16:
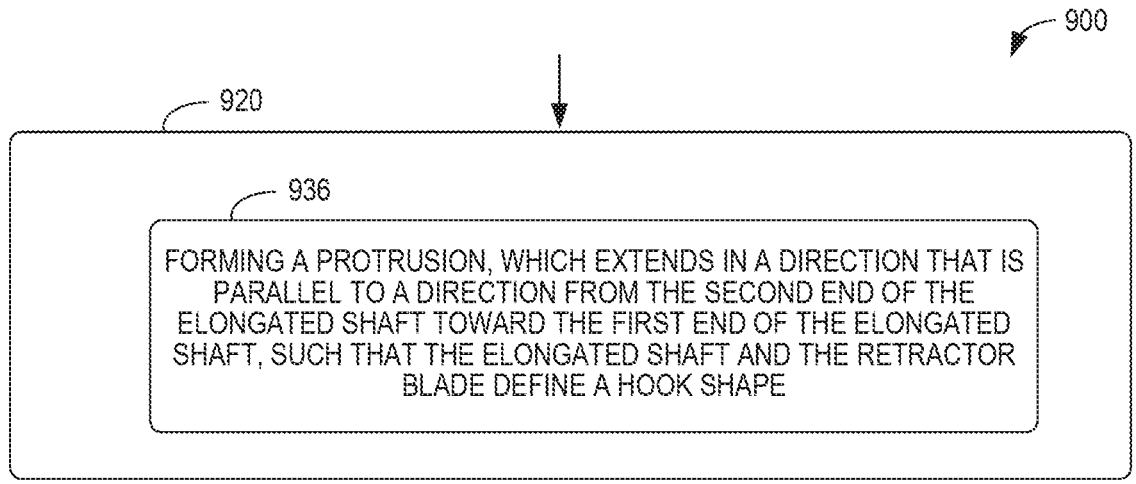
FIG. 16 depicts a flowchart for a method retracting tissue that can be used with the method shown in FIG. 9, according to an example.

As shown in FIG. 16, forming the retractor blade at block 920 can include forming a protrusion, which extends in a direction that is parallel to a direction from the second end of the elongated shaft toward the first end of the elongated shaft, such that the elongated shaft and the retractor blade define a hook shape at block 936.

Figure 17:
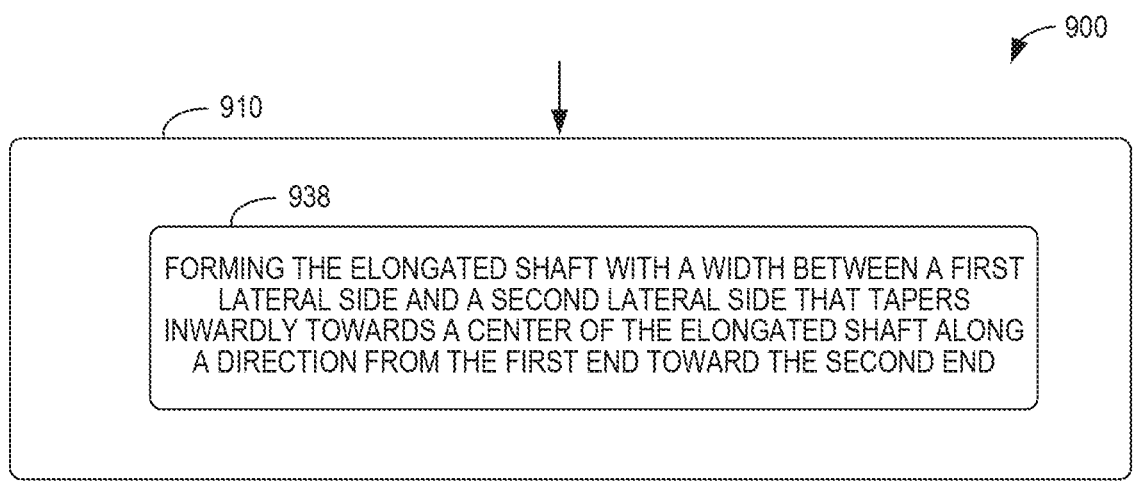
FIG. 17 depicts a flowchart for a method retracting tissue that can be used with the method shown in FIG. 9, according to an example.

As shown in FIG. 17, forming the elongated shaft at block 910 can include forming the elongated shaft with a width between a first lateral side and a second lateral side that tapers inwardly towards a center of the elongated shaft along a direction from the first end toward the second end at block 938.

Figure 18:
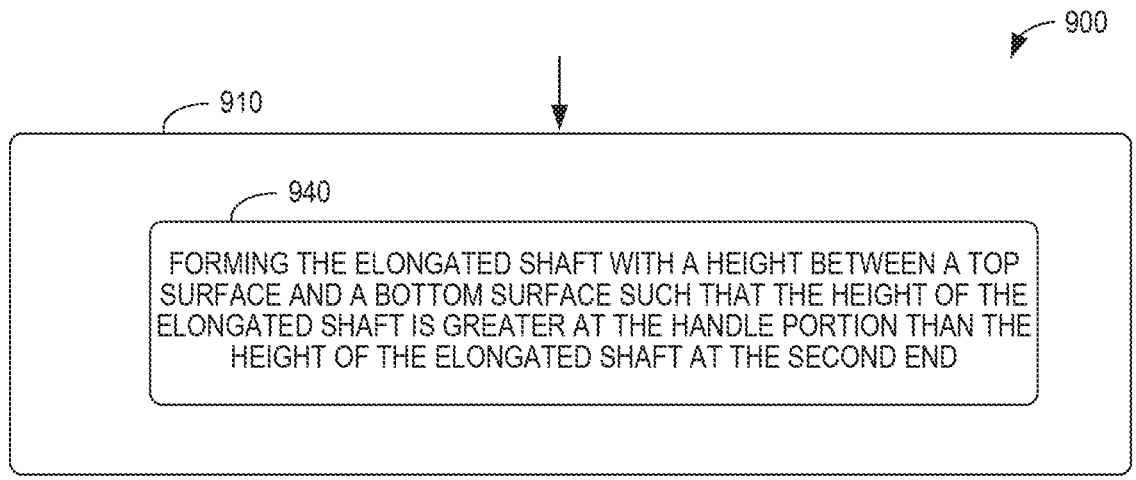
FIG. 18 depicts a flowchart for a method retracting tissue that can be used with the method shown in FIG. 17, according to an example.

As shown in FIG. 18, forming the elongated shaft at block 910 can include forming the elongated shaft with a height between a top surface and a bottom surface such that the height of the elongated shaft is greater at the handle portion than the height of the elongated shaft at the second end at block 940.

Figure 19:
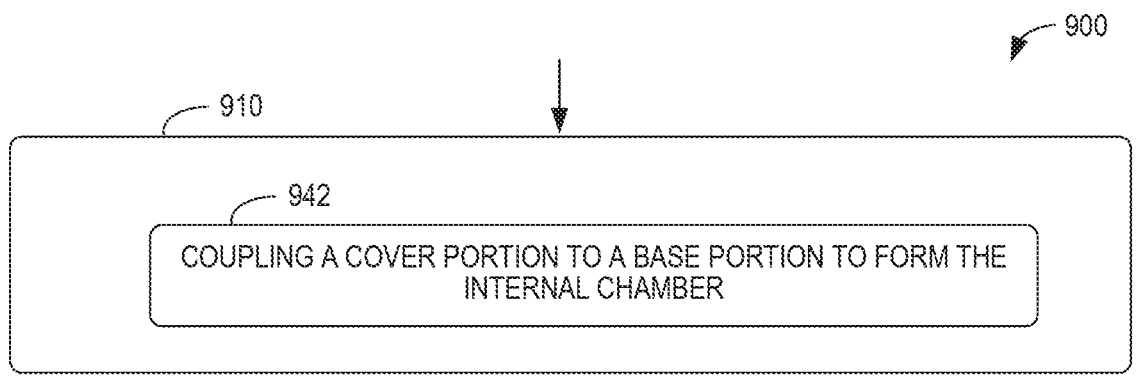
FIG. 19 depicts a flowchart for a method retracting tissue that can be used with the method shown in FIG. 9, according to an example.

As shown in FIG. 19, forming the elongated shaft at block 910 can include coupling a cover portion to a base portion to form the internal chamber at block 942.

Figure 20:
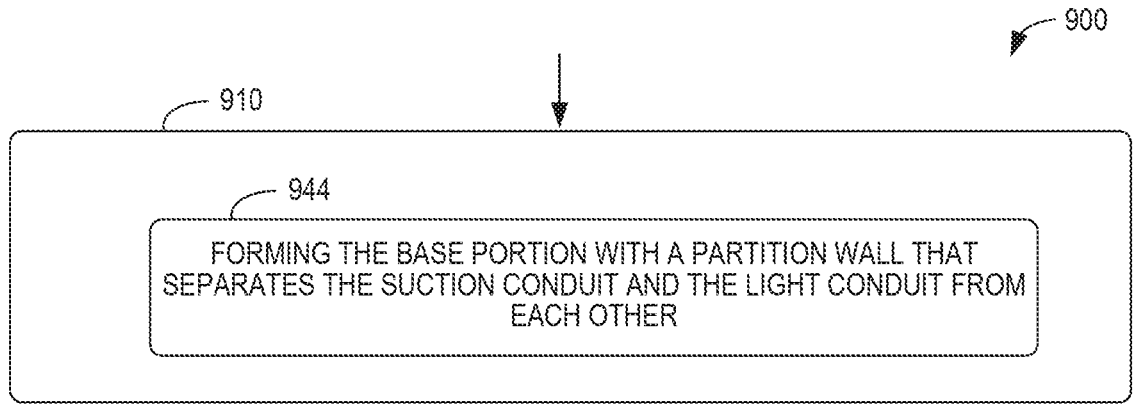
FIG. 20 depicts a flowchart for a method retracting tissue that can be used with the method shown in FIG. 19, according to an example.

As shown in FIG. 20, forming the elongated shaft at block 910 can include forming the base portion with a partition wall that separates the suction conduit and the light conduit from each other at block 944.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. A surgical retractor, comprising:
an elongated shaft extending from a first end to a second end, wherein the elongated shaft defines an internal chamber, wherein the elongated shaft comprises:
a handle portion at the first end of the elongated shaft,
a suction conduit in a first lateral portion of the internal chamber, wherein the suction conduit extends from a suction port at the first end to a suction aperture at the second end,
a light conduit in a second lateral portion of the internal chamber, wherein the light conduit extends from a light-input port at the first end to a light aperture at the second end,
wherein the suction conduit and the light conduit are substantially coplanar between the first end and the second end;
a retractor blade extending from the second end of the elongated shaft; and
an optical waveguide in the light conduit of the elongated shaft.

2. The surgical retractor of claim 1, wherein the light-input port is configured to couple a light source to the optical waveguide in the light conduit.

3. The surgical retractor of claim 1, wherein the suction conduit is configured to apply a vacuum to the suction aperture when the suction port is coupled to a vacuum source.

4. The surgical retractor of claim 1, wherein the suction conduit is fluidly sealed from the light conduit.

5. The surgical retractor of claim 1, wherein the elongated shaft bends towards the retractor blade at the second end of the elongated shaft such that the suction aperture and the light aperture are configured to face a surgical site when the retractor blade retracts tissue.

6. The surgical retractor of claim 5, wherein the suction aperture and the light aperture are coplanar.

7. The surgical retractor of claim 5, wherein the retractor blade comprises a back surface and a front surface opposite the back surface, wherein the second end of the elongated shaft is positioned in front of the front surface of the retractor blade.

8. The surgical retractor of claim 1, wherein the retractor blade comprises a proximal portion and a distal portion, wherein the proximal portion is wider than the distal portion.

9. The surgical retractor of claim 8, wherein the proximal portion of the retractor blade has a shape that tapers inwardly along a direction from the elongated shaft toward the distal portion of the retractor blade.

10. The surgical retractor of claim 8, wherein the retractor blade has a length in a dimension between the elongated shaft and a distal-most end of the retractor blade, and
wherein the proximal portion comprises at least 25 percent of the length of the retractor blade.

11. The surgical retractor of claim 1, wherein the retractor blade comprises a protrusion, which extends in a direction that is parallel to a direction from the second end of the elongated shaft toward the first end of the elongated shaft, such that the elongated shaft and the retractor blade define a hook shape.

12. The surgical retractor of claim 1, wherein a longitudinal axis of the elongated shaft is at an angle relative to a longitudinal axis of the retractor bade, and
wherein the angle is between approximately 45 degrees and approximately 135 degrees.

13. The surgical retractor of claim 1, wherein the elongated shaft has a width between a first lateral side and a second lateral side that tapers inwardly towards a center of the elongated shaft along a direction from the first end toward the second end.

14. The surgical retractor of claim 13, wherein the elongated shaft has a height between a top surface and a bottom surface, wherein the height of the elongated shaft is greater at the handle portion than the height of the elongated shaft at the second end.

15. The surgical retractor of claim 1, wherein the elongated shaft comprises a cover portion coupled to a base portion, wherein the internal chamber is defined by the cover and the base portion.

16. The surgical retractor of claim 15, wherein the base portion comprises a partition wall that separates the suction conduit and the light conduit from each other.

17. The surgical retractor of claim 1, wherein the optical waveguide is a non-fiber optic waveguide.

18. The surgical retractor of claim 17, wherein the optical waveguide extends from a first-waveguide end to a second-waveguide end,
wherein the optical waveguide has a first cross-sectional area at the first-waveguide end,
wherein the optical waveguide has a second cross-sectional area at the second-waveguide end,
wherein the optical waveguide has a third cross-sectional area at an intermediate between the first-waveguide end and the second-waveguide end, and
wherein the third cross-sectional area is less than the first cross-sectional area and the second cross-sectional area.

19. The surgical retractor of claim 18, wherein a center axis of the optical waveguide is non-linear such that the first-waveguide end of the optical waveguide is laterally offset relative to the second-waveguide end of the optical waveguide.

20. The surgical retractor of claim 1, wherein the optical waveguide comprises a bend at the second end of the elongated shaft.

* * * * *